US007132505B1

(12) United States Patent
Lazdunski et al.

(10) Patent No.: US 7,132,505 B1
(45) Date of Patent: Nov. 7, 2006

(54) POLYPEPTIDE INHIBITING A PROTON-GATED NA+ CHANNEL, A NUCLEIC ACID CODING FOR SUCH POLYPEPTIDE AND A METHOD OF MANUFACTURING AN ASIC1A CHANNEL BLOCKER

(75) Inventors: Michel Lazdunski, Nice (FR); Pierre Escoubas, Valbonne (FR); Jan DeWeille, LeBar s/Loup (FR); Sylvie Diochot, Saint Laurent du Var (FR)

(73) Assignee: Centre National de la Recherche Scientifique - CNRS (FR)

( * ) Notice: Subject to any disclaimer, the term of this patent is extended or adjusted under 35 U.S.C. 154(b) by 1219 days.

(21) Appl. No.: 09/852,378

(22) Filed: May 10, 2001

(51) Int. Cl.
*C07K 14/00* (2006.01)

(52) U.S. Cl. ...................... 530/324; 530/300; 530/344; 514/2; 514/21

(58) Field of Classification Search ..................... None
See application file for complete search history.

(56) References Cited

OTHER PUBLICATIONS

Bowie et al. (1990) Science 247:1306-1310.*

Waldmann, R., Champigny, G., Bassilana, F., Heurteaux, C. and Lazdunski, M. "A Proton-Gated Cation Channel Involved in Acid-Sensing", Nature, 386, 173-177, 1997.

Chen, C.C., England, S., Akopian, A.N and Wood, J.N., "a Sensory Neuron-Specific, Proton-Gated Ion Channel" , Proc. Natl. Acad. Sci. USA, 95, 10240-10245, 1998.

Price, M.P., Snyder, P.M. and Welsh, M.J., "Cloning and Expression of a Novel Human Brain Na+ Channel", J. Biol. Chem., 271, 7879-7882, 1996.

Lingueglia, E., de Weille, J.R., Bassilana, F., Heurteaux, C., Sakal, H., Waldmann, R. and Lazdunski, M., "a Modulatory Subunit of Acid Sensing Ion Channels in Brain and Dorsal Root Ganglion Cells", J. Biol. Chem., 272, 29778-29783, 1997.

Waldmann, R., Bassilana, F., de Weille, J., Champigny, G., Heurteaux, C. and Lazdunski, M., "Molecular Cloning of a Non-Inactivating Proton-Gated Na+ Channel Specific for Sensory Neurons", J. Biol. Chem., 272, 20975-209758, 1997.

Hucho, F. (1995), "Toxins as tools in neurochemistry", Ang. Chem. Int. Ed. Eng., 34, 39-50.

Narasimhan, L., Singh, Jr., Humblet, C. Guruprasad, K. and Blundell, T., "Snail and Spider Toxins Share a Similar Tertiary Structure and 'Cystine Motif'", Nat. Struct. Biol., 1, 850-852, 1994.

Pallaghy, P.K., Nielsen, K.J., Cralk, D.J. and Norton, R.S., "A Common Structural Motif Incorporating a Cystine Knot and a Triple-stranded Beta-sheet in Toxic and Inhibitory Polypeptides", Protein Sci., 3, 1833-1839, 1994).

Norton, R.S. and Pallaghy, P.K., "The Cystine Knot Structure of Ion Channel Toxins and Related Polypeptides", Toxicon, 36 1573-1583, 1988.

* cited by examiner

*Primary Examiner*—Michael Pak
(74) *Attorney, Agent, or Firm*—DLA Piper US LLP

(57) ABSTRACT

The invention relates to a substantially pure polypeptide functioning as an ASIC1a channel blocker. Also provided is a nucleic acid molecule coding such polypeptide, pharmaceutical composition containing such polypeptide and a method of manufacturing an ASIC1a channel blocker.

12 Claims, 5 Drawing Sheets

Fig 1

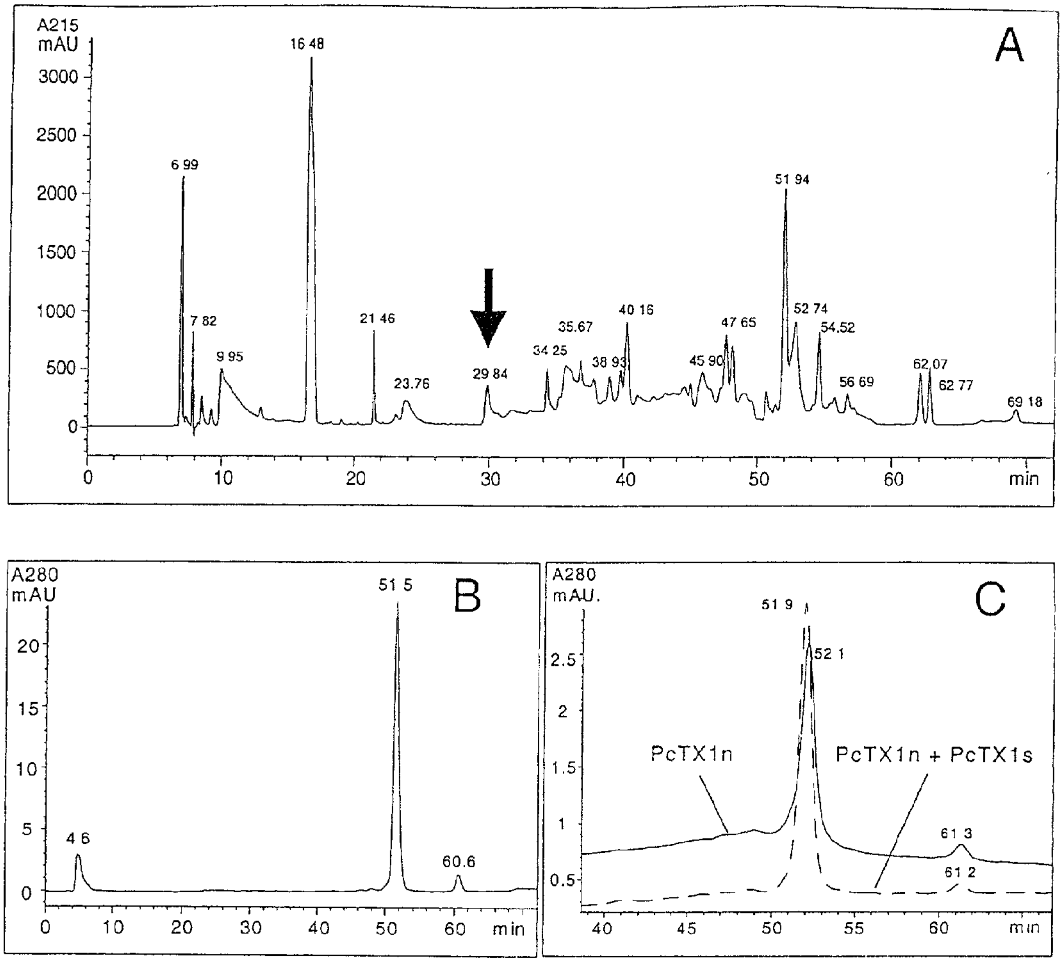

D

```
PcTX1          EDCIPKWKGCVNRHGDCCEGLECWKRRRSFEVCVPKTPKT
Edman          -----------------------------X----->
BNP-skatole                                KRRRSFEVCVPKTPKT
Trypsin No7                                    XXEVCVP
V8                                               VCVPKTPKT
```

E

```
                                                                    % Sim  Activity
PcTX1    ----EDCIPKWKGCVNRHG-DCCEGLECWKRRRSFEVCVPKTPKT-                  ASIC1a
HpTX2    ----DDCGKLFSGCDTNA--DCCEGYVCRL-------WCKLDW----           59.5  Kv4.2
HaTX1    -----ECRYLFGGCKTTS--DCCKHLGCKFR---DKYCAWDFTFS-            59.8  Kv2.1
SNX482   GVDKAGCRYMFGGCSVND--DCCPRLGCHSL---FSYCAWDLTFSD            60.0  VSCC (R)
GsTXSIA  -----DCVRFWGKCSQTS--DCCPHLACKSKW-PRNICVWDGSV--            68.9  VSCC (P/N)
PaTX1    -----YCQKWMWTCDSAR--KCCEGLVCRL-------WCKKII----           55.6  Kv4.2/4.3
```

F

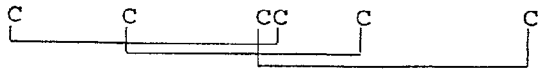

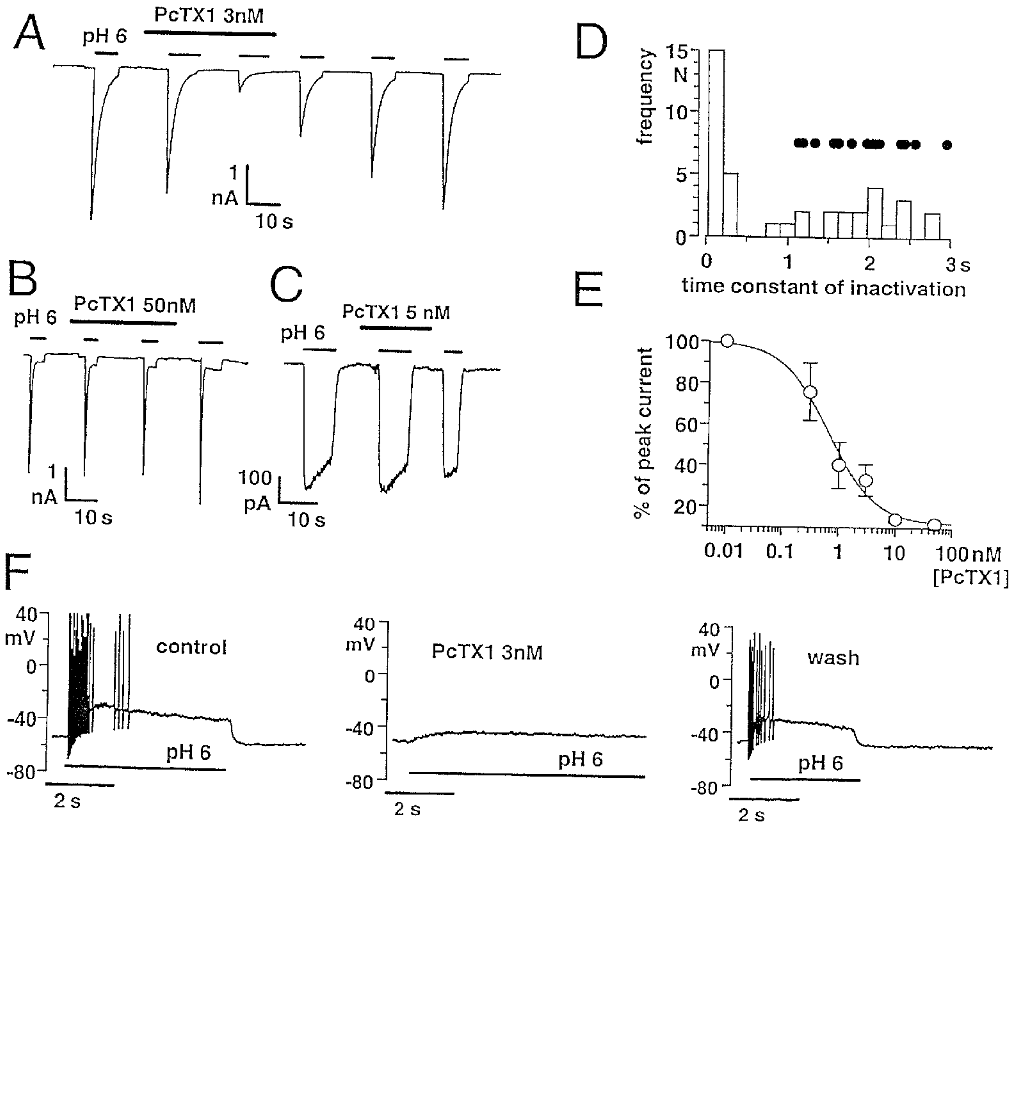
A
pH 6
PcTX1 3nM
1 nA
10 s
D
15 N
10
5
0
frequency
0
1
2
3 s
time constant of inactivation
B
pH 6
PcTX1 50nM
1 nA
10 s
C
pH 6
PcTX1 5 nM
100 pA
10 s
E
100
80
60
40
20
% of peak current
0.01
0.1
1
10
100nM
[PcTX1]
F
40 mV
0
-40
-80
control
pH 6
2 s
PcTX1 3nM
wash

SEQUENCE LISTING

```
<160> NUMBER OF SEQ ID NOS: 10

<210> SEQ ID NO 1
<211> LENGTH: 40
<212> TYPE: PRT
<213> ORGANISM: Psalmopoeus sp.
```

-continued

<400> SEQUENCE: 1

```
Glu Asp Cys Ile Pro Lys Trp Lys Gly Cys Val Asn Arg His Gly Asp
  1               5                  10                  15

Cys Cys Glu Gly Leu Glu Cys Trp Lys Arg Arg Arg Ser Phe Glu Val
             20                  25                  30

Cys Val Pro Lys Thr Pro Lys Thr
         35                  40
```

<210> SEQ ID NO 2
<211> LENGTH: 36
<212> TYPE: PRT
<213> ORGANISM: Psalmopoeus sp.
<220> FEATURE:
<221> NAME/KEY: MOD_RES
<222> LOCATION: (31)
<223> OTHER INFORMATION: Variable amino acid

<400> SEQUENCE: 2

```
Glu Asp Cys Ile Pro Lys Trp Lys Gly Cys Val Asn Arg His Gly Asp
  1               5                  10                  15

Cys Cys Glu Gly Leu Glu Cys Trp Lys Arg Arg Arg Ser Phe Xaa Val
             20                  25                  30

Cys Val Pro Lys
         35
```

<210> SEQ ID NO 3
<211> LENGTH: 16
<212> TYPE: PRT
<213> ORGANISM: Psalmopoeus sp.

<400> SEQUENCE: 3

```
Lys Arg Arg Arg Ser Phe Glu Val Cys Val Pro Lys Thr Pro Lys Thr
  1               5                  10                  15
```

<210> SEQ ID NO 4
<211> LENGTH: 7
<212> TYPE: PRT
<213> ORGANISM: Psalmopoeus sp.
<220> FEATURE:
<221> NAME/KEY: MOD_RES
<222> LOCATION: (1)..(2)
<223> OTHER INFORMATION: Variable amino acid

<400> SEQUENCE: 4

```
Xaa Xaa Glu Val Cys Val Pro
  1               5
```

<210> SEQ ID NO 5
<211> LENGTH: 9
<212> TYPE: PRT
<213> ORGANISM: Psalmopoeus sp.

<400> SEQUENCE: 5

```
Val Cys Val Pro Lys Thr Pro Lys Thr
  1               5
```

<210> SEQ ID NO 6
<211> LENGTH: 30
<212> TYPE: PRT
<213> ORGANISM: Psalmopoeus sp.

<400> SEQUENCE: 6

```
Asp Asp Cys Gly Lys Leu Phe Ser Gly Cys Asp Thr Asn Ala Asp Cys
```

-continued

```
 1               5                   10                  15

Cys Glu Gly Tyr Val Cys Arg Leu Trp Cys Lys Leu Asp Trp
             20                  25                  30


<210> SEQ ID NO 7
<211> LENGTH: 35
<212> TYPE: PRT
<213> ORGANISM: Psalmopoeus sp.

<400> SEQUENCE: 7

Glu Cys Arg Tyr Leu Phe Gly Gly Cys Lys Thr Thr Ser Asp Cys Cys
 1               5                   10                  15

Lys His Leu Gly Cys Lys Phe Arg Asp Lys Tyr Cys Ala Trp Asp Phe
             20                  25                  30

Thr Phe Ser
         35


<210> SEQ ID NO 8
<211> LENGTH: 41
<212> TYPE: PRT
<213> ORGANISM: Psalmopoeus sp.

<400> SEQUENCE: 8

Gly Val Asp Lys Ala Gly Cys Arg Tyr Met Phe Gly Gly Cys Ser Val
 1               5                   10                  15

Asn Asp Asp Cys Cys Pro Arg Leu Gly Cys His Ser Leu Phe Ser Tyr
             20                  25                  30

Cys Ala Trp Asp Leu Thr Phe Ser Asp
         35                  40


<210> SEQ ID NO 9
<211> LENGTH: 36
<212> TYPE: PRT
<213> ORGANISM: Psalmopoeus sp.

<400> SEQUENCE: 9

Asp Cys Val Arg Phe Trp Gly Lys Cys Ser Gln Thr Ser Asp Cys Cys
 1               5                   10                  15

Pro His Leu Ala Cys Lys Ser Lys Trp Pro Arg Asn Ile Cys Val Trp
             20                  25                  30

Asp Gly Ser Val
         35


<210> SEQ ID NO 10
<211> LENGTH: 29
<212> TYPE: PRT
<213> ORGANISM: Psalmopoeus sp.

<400> SEQUENCE: 10

Tyr Cys Gln Lys Trp Met Trp Thr Cys Asp Ser Ala Arg Lys Cys Cys
 1               5                   10                  15

Glu Gly Leu Val Cys Arg Leu Trp Cys Lys Lys Ile Ile
             20                  25
```

POLYPEPTIDE INHIBITING A PROTON-GATED NA+ CHANNEL, A NUCLEIC ACID CODING FOR SUCH POLYPEPTIDE AND A METHOD OF MANUFACTURING AN ASIC1A CHANNEL BLOCKER

FIELD OF THE INVENTION

This invention pertains to a substantially pure polypeptide functioning as an ASIC1a channel blocker. More particularly, this polypeptide has the amino acid sequence represented by SEQ ID No.1. Also provided is a nucleic acid coding for such polypeptide and a method of manufacturing an ASIC1a channel blocker.

BACKGROUND

Proton-gated $Na^+$-permeable channels are the simplest form of ligand-gated channels. They are present in many neuronal cell types throughout the central nervous system, suggesting an important function of these channels in signal transduction associated with local pH variations during normal neuronal activity. These channels might also play an important role in pathological situations such as brain ischemia or epilepsy which produce significant extracellular acidification. They are also present in nociceptive neurons and are thought to be responsible for the sensation of pain that accompanies tissue acidosis in muscle and cardiac ischemia, corneal injury, and in inflammation and local infection.

It is only very recently that the first proton-gated channel, ASIC (for Acid Sensitive Ion Channel) was cloned (Waldmann, R., Champigny, G., Bassilana, F., Heurteaux, C. and Lazdunski, M. "A Proton-Gated Cation Channel Involved in Acid-Sensing", *Nature,* 386, 173–177, 1997.) The ASICs belong to a superfamily which includes amiloride-sensitive epithelial $Na^+$ channels (ENaCs), the FMRFamide-gated $Na^+$ channel (FaNaC) and the nematode degenerins (DEGs), which probably correspond to mechano-sensitive $Na^+$-permeable channels. Several ASIC subunits have now been described: ASIC1a (Waldmann, R., above) and ASIC1b (Chen, C. C., England, S., Akopian, A. N. and Wood, J. N., "a Sensory Neuron-Specific, Proton-Gated Ion Channel", *Proc. Natl. Acad. Sci. USA,* 95, 10240–10245, 1998), ASIC2a (Price, M. P., Snyder, P. M. and Welsh, M. J., "Cloning and Expression of a Novel Human Brain $Na^+$ Channel", *J. Biol. Chem.,* 271, 7879–7882, 1996) and ASIC2b (Lingueglia, E., de Weille, J. R., Bassilana, F., Heurteaux, C., Sakai, H., Waldmann, R. and Lazdunski, M., "a Modulatory Subunit of Acid Sensing Ion Channels in Brain and Dorsal Root Ganglion Cells", *J. Biol. Chem.,* 272, 29778–29783, 1997), ASIC3 (Waldmann, R., Bassilana, F., de Weille, J., Champigny, G., Heurteaux, C. and Lazdunski, M., "Molecular Cloning of a Non-Inactivating Proton-Gated $Na^+$ Channel Specific for Sensory Neurons", *J. Biol. Chem.,* 272, 20975–209758, 1997). The different subunits produce channels with different kinetics, external pH sensitivities and tissue distribution. They can form functional homomultimers as well as heteromultimers.

ASIC1a and ASIC1b both mediate rapidly inactivating currents following rapid and modest acidification of the external pH. However, while ASIC1a is present in both brain and afferent sensory neurons, its splice variant ASIC1b, is found only in sensory neurons. ASIC2a forms an active $H^+$-gated channel and is abundant in the brain, but essentially absent in sensory neurons while its splice variant ASIC2b is present in both brain and sensory neurons and is inactive as an homomultimer. ASIC2b can form functional heteromultimers with other ASIC subunits and particularly ASIC3. ASIC3 is found exclusively in small sensory neurons which act as nociceptors. Its expression in various heteromultimeric systems generates a biphasic current with a fast inactivating phase followed by a sustained component. The association of ASIC2b with ASIC3 forms an heteromultimer with properties (time course and ionic selectivity) similar to those of a native sustained H+-sensitive channel which is present in dorsal root ganglion cells and appears to play a particularly important role in pain sensation.

Venoms from snakes, scorpions, sea anemones, marine snails and spiders are rich sources of peptide toxins which have proven of great value in the functional exploration of voltage-sensitive and ligand-gated ion channels (Hucho, F. (1995), "Toxins as tools in neurochemistry", *Ang. Chem. Int. Ed. Eng.,* 34, 39–50). Nevertheless, there is a continuing need to find new materials which affect these channels.

SUMMARY OF THE INVENTION

This invention relates to a substantially pure polypeptide functioning as an ASIC1a channel blocker, a nucleic acid molecule including an encoding nucleic sequence for a polypeptide, a polyclonal or monoclonal antibody directed against a polypeptide and a derivative or a fragment of these, a vector comprising at least one molecule of nucleic acid and adapted control sequences, a cellular host transformed by one molecule of nucleic acid, a nucleic or oligonucleoide probe prepared from one molecule of nucleic acid and a pharmaceutical composition containing a polypeptide or pharmaceutically-acceptable salts thereof and a pharmaceutically-acceptable carrier.

This invention also relates to a method of manufacturing an ASIC1a channel blocker including the steps of obtaining at least one *Psalmopeous cambridgei* spider, obtaining venom from the spider by electrically milking the spider, separating toxins of the venom by reversed-phase chromatography, further separating components of said venom by cation exchange chromatography, recovering and isolating separated toxins of the venom and combining the isolated toxin with a pharmaceutically acceptable carrier such that the toxin is capable of functioning as an ASIC1a channel blocker.

BRIEF DESCRIPTION OF THE DRAWINGS

Other advantages and characteristics of the invention will become apparent by reading the following examples concerning the purification, the peptide characterization and the effect of PcTX1 on the activity of ASIC1a, ASIC1b, ASIC2a and ASIC3 channels and which refer to the attached drawings in which:

FIG. 1 has several parts relating to the purification and characterization of PcTX1. Part A is a graphical depiction of a reversed-phase HPLC separation of crude *Psalmopoeus cambridgei* venom. Part B is a graphical depiction of cation-exchange chromatography of the reversed-phase HPLC fraction containing PcTX1. Part C is a graphical depiction of cation-exchange chromatography of PcTX1n and PcTX1n+PcTX1s. Part D shows the sequence of PcTX1s and fragments thereof. Part E is a comparison of PcTX1 and short spider peptides of similar structure and known mode of action. Part F shows the conserved disulfide bridges in PcTX1.

FIG. 4 has several parts relating to the effect of PcTX1 on a subpopulation of $H^+$-gated currents in dorsal root ganglion neurons. Part A shows inhibition of $H^+$-gated currents by PcTX1 in 23 of 48 neurons. Part B shows the effect of PcTX1 on a portion of the remaining 25 of 48 neurons which were not responsive. Part C shows the effect of PcTX1 on a portion of the remaining 25 of 48 neurons which were not responsive. Part D is a profile of the distribution of time constants in different cells. Part E is a graph showing a dose-inhibition curve obtained from cells expressing the PcTX1-sensitive channels. Part F is a graph showing the suppression of activity in DRG neurons by PcTX1.

FIG. 5. Part A is a graphical representation of the current inhibition in cerebellar granule cells by PcTX1. Part B is a graph showing the pH-dependence of proton-gated current in cerebellar cells.

DETAILED DESCRIPTION

Figure 2:
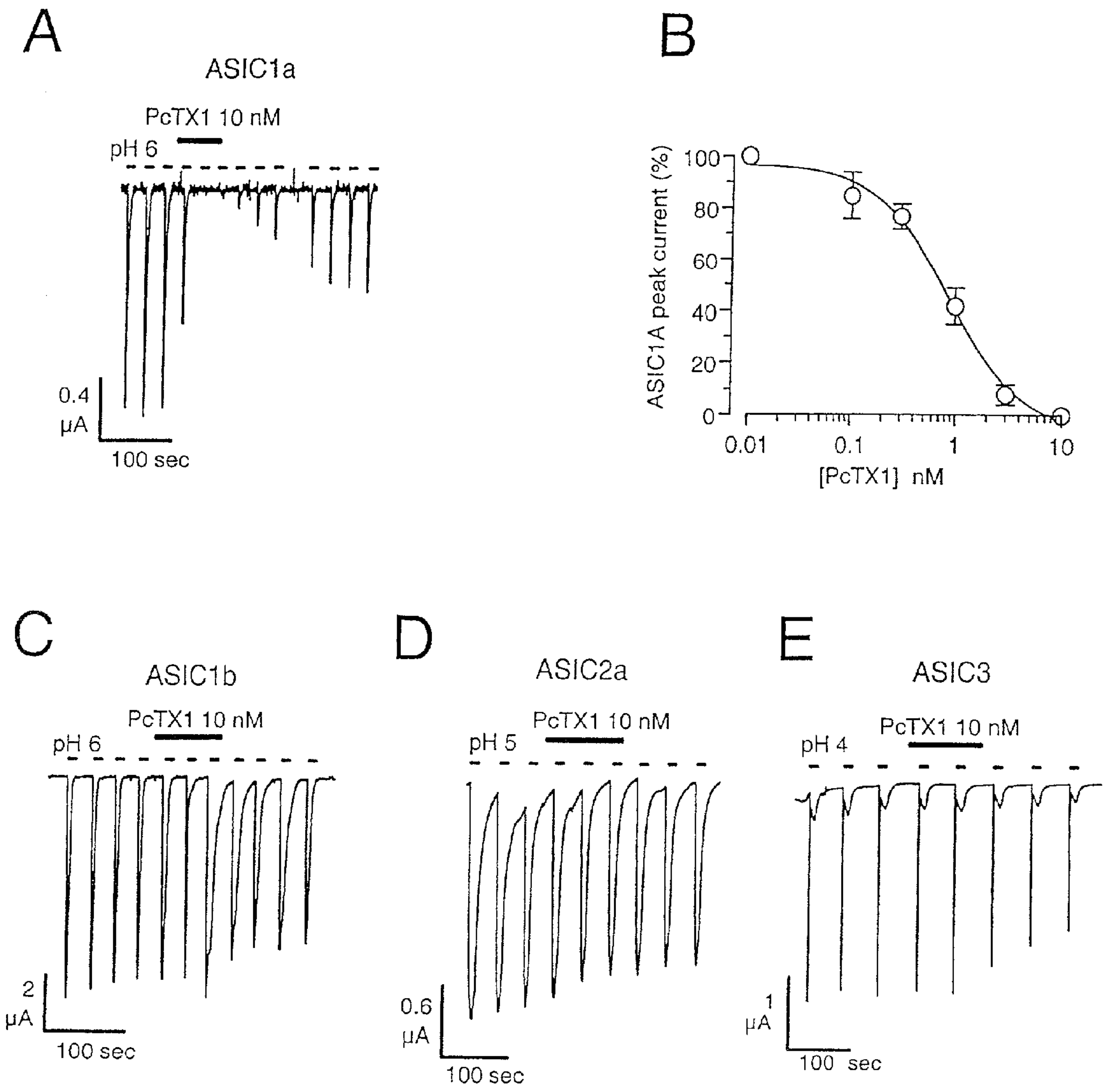
FIG. 2 has several parts which relate to the selective blocking of $H^+$-gated channels by PcTX1. Part A is a graphical representation of the effect of 10 nM PcTX1 on ASIC1a current. Part B is a graph showing the close-response curve for synthetic PcTX1 block of ASIC1a current with a pH drop from 7.4 to 6. Part C is a graphical representation of the effect of 1 nM PcTX1 on ASIC1b current with pH drop from 7.4 to 6. Part D is a graphical representation of the effect of 10 nM PcTX1 on ASIC2a current. Part E is a graphical representation of the effect of 10 nM PcTX1 on ASIC3 current.

The Inventors have identified and characterized the first potent and specific blocker of the ASIC1a channels, from the venom of the South-American tarantula *Psalmopoeus cambridgei*. This first potent and specific blocker of the ASIC1a channels is called hereafter Psalmotoxin 1 (PcTX1).

The molecular scaffold of PcTX1 is likely to be similar to that previously described for both cone snail and spider toxins (Narasimhan, L., Singh, Jr., Humblet, C. Guruprasad, K. and Blundell, T., "Snail and Spider Toxins Share a Similar Tertiary Structure and 'Cystine Motif'", *Nat. Struct. Biol.,* 1, 850–852, 1994; Pallaghy, P. K., Nielsen, K. J., Craik, D. J. and Norton, R. S., "A Common Structural Motif Incorporating a Cystine Knot and a Triple-stranded Beta-sheet in Toxic and Inhibitory Polypeptides", *Protein Sci.,* 3, 1833–1839, 1994). It comprises a triple-stranded antiparallel beta-sheet structure reticulated by three disulfide bridges, and tightly folded into the "knottin" fold pattern (Norton, R. S. and Pallaghy, P. K., "The Cystine Knot Structure of Ion Channel Toxins and Related Polypeptides", *Toxicon,* 36, 1573–1583, 1988). PcTX1 is characterized by the unusual quadruplet $Lys_{25}$, $-Arg_{26}$-$Arg_{27}$-$Arg_{28}$, which probably forms a strongly positive "patch" at the surface of the toxin molecule, constituting an area which is a strong candidate for receptor recognition.

PcTX1 is specific for ASIC1a and can distinguish between the two ASIC1 splice variants ASIC1a and ASIC1b although they only differ in their N-terminal sequence. PcTX1 can also distinguish between ASIC1a, ASIC2 and ASIC3. Furthermore, PcTX1 loses its capacity to block ASIC1a as soon as this subunit is associated with another member of the family, be it ASIC2a or ASIC3.

An important site of the interaction of ASIC1a with PcTX1 is believed to be located in the extracellular stretch of 113 amino acids situated immediately after the first transmembrane domain. This is the only extracellular site in which there are differences between ASIC1a and ASIC1b.

ASIC1a is present in the central nervous system (notably in the hippocampus and the cerebellar granular layer) as well as in DRG neurons. Electrophysiological experiments have shown that both cerebellar granule cells and a sub-population of DRG neurons possess $H^+$-gated currents that inactivate at pH 6 with time constants of 1.95–2.06 s. This is very similar if not identical to the time constant of inactivation (2.10±0.30 s) of the homomultimeric ASIC1a current expressed in COS cells. The $H^+$-gated currents in these neurons are inhibited by very low concentrations of PcTX1. The resemblance in the inactivation kinetics and pH-dependence, in the selective block of the current by PcTX1 and the near identity of the $IC_{50}$ values for the blockade of ASIC1a channels ($IC_{50}$=0.9 nM) and of native channels ($IC_{50}$=0.7 nM) strongly suggests that the $H^+$-gated current with a $\tau_{inact}$ of ~2 s in both DRG cells and cerebellar granular cells is mediated by an homomultimeric assembly of ASIC1a. This view is strengthened by the fact that none of the heteromultimeric channels tested (ASIC1a/ASIC2a and ASIC1a/ASIC3) is sensitive to the toxin.

DRG neurons also express H-gated currents with time constants of inactivation that are either faster or slower than the time constant of inactivation of the homomultimeric ASIC1a current. A class of these proton-sensitive channels inactivates at a fast rate ($\tau_{inact}$=0.24±0.03 s) which is very similar to the rate of inactivation of the ASIC1a/ASIC3 channel expressed in COS cells ($\tau_{inact}$=0.19±0.01 s). This rapidly inactivating current, like the current generated by ASIC1a/ASIC3 heteromultimers, is insensitive to PcTX1. Therefore, it is likely that the fast inactivating $H^+$-gated $Na^+$ channel in DRG neurons is the ASIC1a/ASIC3 heteromultimer.

The ASIC3 current alone or in association with ASIC2b corresponds to the maintained current recorded in DRG cells. Neither ASIC3 homomultimers, ASIC3/ASIC2b heteromultimers nor the native non-activating $H^+$-gated channels are blocked by PcTX1.

Spider venoms are cocktails of neuroactive peptides capable of incapacitating their prey through a myriad of molecular mechanisms. PcTX1 is a potent tool which now opens the way to a more detailed analysis of the physiological function of the important class of $H^+$-gated $Na^+$ channels.

Thus, the invention concerns a substantially pure polypeptide functioning as an ASIC1a channel blocker. The invention concerns more particularly a substantially pure polypeptide functioning as an ASIC1a channel blocker extracted from the venom of the South-American tarantula *Psalmopoeus cambridgei*. This polypeptide functioning as an ASIC1a channel blocker has advantageously a calculated molecular weight of about 4689 Da. The effects of the polypeptide functioning as an ASIC1a channel blocker are advantageously reversible.

Preferably, the polypeptide functioning as an ASIC1a channel blocker comprises the following amino acid sequence:

EDCIPKWKGCVNRHGDCCE-
GLECWKRRRSFEVCVPKTPKT represented by SEQ ID No.1 and pharmaceutically-acceptable salts thereof.

The invention concerns a nucleic acid molecule comprising or constituted of an encoding nucleic sequence for a polypeptide functioning as an ASIC1a channel blocker. The invention also concerns a nucleic acid molecule which encodes for a polypeptide functioning as an ASIC1a channel blocker whose amino acid sequence is represented by SEQ ID No. 1.

Another aspect of the invention is polyclonal or monoclonal antibodies directed against a polypeptide functioning as an ASIC1a channel blocker of the invention, a derivative or a fragment of these. These antibodies can be prepared by methods described in the literature. According to prior art techniques, polyclonal antibodies are formed by the injection of proteins, extracted from the epithelium or produced by genetic transformation of a host, into animals, and then recuperation of antiserums and antibodies from the antiserums for example by affinity chromatography. The monoclonal antibodies can be produced by fusing myeloma cells with spleen cells from animals previously immunised using the receptors of the invention. These antibodies are useful in the search for new polypeptides functioning as an ASIC1a channel blocker or the homologues of this polypeptide in other species.

The invention also concerns a vector comprising at least one molecule of the nucleic acid described above, advantageously associated with adapted control sequences, together with a production or expression process in a cellular host of a polypeptide functioning as an ASICL a channel blocker of the invention or a fragment thereof. The preparation of these vectors as well as the production or expression in a protein host of the invention can be carried out by molecular biology and genetic engineering techniques well known to those skilled in the art.

An encoding nucleic acid molecule for a polypeptide functioning as an ASIC1a channel blocker or a vector according to the invention can also be used to transform animals and establish a line of transgenic animals. The vector used is chosen as a function of the host into which it is to be transferred. It can be any vector such as a plasmid. Thus, the invention also relates to cellular hosts expressing a polypeptide functioning as an ASIC1a channel blocker obtained in conformity with the preceding processes.

The invention also relates to nucleic and oligonucleotide probes prepared from the molecules of nucleic acid according to the invention. These probes, marked advantageously, are useful for hybridisation detection of similar polypeptide functioning as an ASIC1a channel blocker in other individuals or species. According to prior art techniques, these probes are put into contact with a biological sample. Different hybridisation techniques can be used, such as Dot-blot hybridisation or replica hybridisation (such as Southern technique) or other techniques (such as DNA chips). The oligonucleotide probes are useful for PCR experiments, for example, to search for genes in other species or with a diagnostic aim.

Another aspect of this invention is a pharmaceutical composition containing a polypeptide functioning as an ASIC1a channel blocker or pharmaceutically-acceptable salts thereof and a pharmaceutically-acceptable carrier.

The invention also relates to a method of manufacturing an ASIC1a channel blocker comprising the steps of:

(a) obtaining at least one *Psalmopoeus cambridgei* spider;

(b) obtaining venom from said at least one spider by electrically milking said at least one spider;

(c) separating components of the venom by reversed-phase chromatography such that toxins of the venom are separated;

(d) further separating the components of the venom by cation exchange chromatography;

(e) recovering and isolating the separated toxins of the venom; and (f) combining the isolated toxin with a pharmaceutically acceptable carrier such that the toxin is capable of functioning as an ASIC1a channel blocker.

I. Methods

I.1 Venom and Toxin Purification

*Psalmopoeus cambridgei* (Araneae Theraphosidae) venom was obtained by electrical stimulation of anesthetized spiders (Invertebrate Biologics, Los Gatos, USA). Freeze-dried crude venom was resuspended in distilled water, centrifuged (140000 rpm, 4° C., 20 min), filtered on 0.45 μm microfilters (SJHVL04NS, 4 mm diameter, Millipore, Japan) and stored at −20° C. prior to analysis. Crude venom diluted to ten times the initial volume was fractionated by reversed-phase C8 HPLC (10×250 mm, 5C8MS, Nacalai Tesque, Japan) using a linear gradient of acetonitrile/water in constant 0.1% trifluoroacetic acid (TFA). A second purification step used cation-exchange chromatography on a Tosoh TSK-Gel SP5PW sulfopropyl column (4.6×70 mm) (Tosoh, Japan), with a linear gradient of ammonium acetate in water (20 mM to 2 M). A total of 160 μl of venom was purified, in two separate batches (10 and 150 μl). All solvents used were of HPLC grade. Separation was conducted on a Hewlett-Packard HP1100 system coupled to a diode-array detector and a microcomputer running Chemstation® software. Monitoring of elution was done at 215 and 280 nm.

I.2 Peptide Characterization and Synthesis

I.2.1 Amino-acid Analysis

Samples were hydrolyzed in a Waters Pico-Tag station, with 6N HCl (0.6% phenol) at 110° C., under vacuum for 20 hrs. Hydrolyzed peptides were derivatized with PITC and the derivatized amino-acid mixtures were analyzed by C18RP-HPLC using a gradient of 60% acetonitrile in 50 mM phosphate buffer (100 mM NaClO4).

I.2.2 Sequence Determination

The peptide was reduced and alkylated by 4-vinyl-pyridine, desalted by C8 RP-HPLC and submitted to automated N-terminal sequencing on an Applied Biosystems model 477A gas-phase sequencer.

I.2.3 Enzymatic Cleavages

Reduced-alkylated toxin was submitted to the following treatments: (a) TPCK-treated Trypsin (Sigma Co, USA), 2% w/w, 37° C., 14 h. in 100 mM ammonium bicarbonate, 0.1 mM $CaCl_2$ pH 8.1. (b) V8 protease, 37° C., 24 h. in 50 mM ammonium bicarbonate pH 7.8 in 10% acetonitrile and (c) BNP-skatole (2-(nitrophenylsulfenyl)-3-methyl-3-bromoindolenine), 37° C., 24 h. in 75% acetic acid. Resulting peptides were separated by RP-HPLC using a linear gradient of acetonitrile/water in constant 0.1% TFA.

I.2.4 Mass Spectrometry

Mass spectra of native PcTX1 dissolved in (α-cyano-4-hydroxycinnamic acid (α-CHCA) matrix were recorded on a MALDI-TOF Perseptive Voyager Elite spectrometer (Perseptive Biosystems, USA), in positive ion linear mode using an internal calibration method with a mixture of β-insulin (3495.94 Da) and bovine insulin (5733.5 Da). Data were analyzed using the GRAMS 386 software. Theoretical molecular weights and pI values were calculated from sequence data using the GPMAW protein analysis software (http://130.225-147.138/gpmaw/default.htm). Synthetic PcTX1 was analyzed on a Micromass Platform II electrospray system (Micromass, Altrincharn, UK), in positive mode (cone voltage 20 kV, temperature 60° C.).

I.2.5 Database Searches

Sequence homologies were determined using sequences obtained from a non-redundant search of protein databases, via the BLAST server (blast program http://www.ncbi.nlm-.nih-gov/). Sequence alignments and percentages of similarity were calculated with ClustalW (http://www.caos.k-un.nl/cammsa/CLUSTALW/clustalw.html).

I.2.6 Peptide Synthesis

The synthesis of native PcTX1 was performed using the Fmoc/tert-butyl and maximal temporary protection strategy on an Applied Biosystems 433A synthesizer. The chemical procedure used 0.05 nM of Fmoc-Thr(OtBu)-4-hydroxymethylphenoxy resin (0.39 mmol/g), a 20-fold excess of each amino acid and dicyclohexylcarbodiimide/1-hydroxy-7-aza-benzotriazole activation. Deprotection (1–5 h) and cleavage (200 mg of peptide+resin) were achieved using 10 ml of a mixture of trifluoroacetic acid/triiso-propylsilane/water (9.5/0.25/0.25, v/v/v). The acidic mixture was then precipitated twice in 100 ml of cold diethylether. The solid was dissolved in 50 ml of 10% acetic acid in water, and freeze-dried. The crude reduced toxin was purified by RP-HPLC on a C18 preparative column (21×250 mm, Jupiter) using a 40 min gradient of acetonitrile/water in 0.1% TFA (0% to 18% B in 4 min, 30% B in 30 min, 100% B in 6 min with B: 90% acetonitrile/$H_2O$/0.1% TFA).

Oxidation of the reduced toxin was achieved at 0.1 mg/10 ml in degassed potassium phosphate buffer (100 mM, pH=7.8) using the redox couple reduced glutathione (5 mM)/oxidized glutathione (0.5 mM). The disappearance of the reduced peptide was monitored by RP-HPLC on a C18 analytical column (10×15 mm, Vydac, USA) using a 40 min gradient (0% to 18% B in 8 min, 30% B in 26 min, 60% B in 14 min with B: 90% acetonitrile/$H_2O$/0.1% TFA).

I.3 Electrophysiological Recordings

I.3.1 Expression in *Xenopus* Oocytes

Cloning of cDNA and synthesis of complementary RNA were done as previously described. *Xenopus laevi* were purchased from C.R.B.M. (Montpellier, France). Pieces of the ovary were surgically removed and individual oocytes were dissected in a saline solution (ND96) containing 96 mM NaCl, 2 mM KCl, 1.8 mM $CaCl_2$, 2 mM $MgCl_2$ and 5 mM HEPES (pH 7.4 with NaOH). Stage V and VI oocytes were treated for 2 h with collagenase (1 mg/ml, type Ia, Sigma, USA) in ND96 to remove follicular cells. cRNA (ASIC1a, ASIC2a, Kv2.1, Kv2.2) or DNA (ASICIb, ratASIC3, Kv4.2, Kv4.3) solutions were injected (5 to 10 ng/μl for cRNA and 50 to 100 ng/μl for DNA, 50 nl/oocyte) using a pressure micro injector. The oocytes were kept at 19° C. in the ND96 saline solution supplemented with gentamycin (5 μg/ml). Oocytes were studied within 2 to 4 days following injection of cRNA. In a 0.3 ml perfusion chamber, a single oocyte was impaled with two standard glass micro electrodes (1–2.5 MΩ resistance) filled with 3M KCl and maintained under voltage-clamp using a Dagan TEV 200 amplifier. Stimulation of the preparation, data acquisition and analysis were performed using the pClamp software (Axon Instruments, USA). All experiments were performed at room temperature (21–22° C.) in ND96 0.1% bovine serum albumin was added in solutions containing PcTX1 to prevent its adsorption to tubing and containers. For measurements of ASIC currents, changes in extracellular pH were induced by rapid perfusion, with or without PcTX1, near the oocyte. Test solutions with a pH of 4 or 5 were buffered with MES rather than HEPES. Voltage-dependent $K^+$ channels were activated by depolarization tests to +10 mV from a holding potential of −80 mV and the toxin solutions were applied externally by gently puffing 100 μl near the oocyte.

In the initial screening, 1 μl aliquots of crude venoms were tested at a 1:1000 dilution in ND96 solution. During the fractionation process aliquots (1/10) of chromatographic fractions were dried, redissolved in ND96 and applied to the oocyte by perfusion.

I.3.2 Expression in COS Cells

COS cells, at a density of 20.000 cells per 35 mm diameter petri dish, were transfected with a mix of CD8 and one of the following plasmids: PCI-ASIC1a, PCI-ASIC1b, PCI-ASIC2a, or PCI-ASIC3 (1:5) using the DEAE-Dextran method. Cells were used for electrophysiological measurements one to three days after transfection. Successfully transfected cells were recognized by their ability to fix CD8-antibody-coated beads (Dynal, Norway).

I.3.3 DRG Neurone Cultures

Dorsal root ganglia of 2–3 days old Wistar rats were mechanically dissociated and maintained in culture in Eagle's medium supplemented with 100 ng/ml nerve growth factor. Cells were used for electrophysiological recordings 2 or 3 days after plating.

I.3.4 Cerebellar Granule Cells Cultures

Cerebella of 4 to 8 days old mice were dissected, mechanically dissociated and cultured as described previously. Cells were used for electrophysiological recordings 10–14 days after plating.

I.3.5 Electrophysiology on COS Cells and Neurons

Ion currents were recorded using either the whole-cell or outside-out patch-clamp technique and results stored on hard disk. Data analysis was carried out using Serf freeware (http://ipmc.cnrs.fr/-deweille/serf.html). The statistical significance of differences between sets of data was estimated by the single-sided Student test. The pipette solution contained (in mM): KCl 140, $MgCl_2$ 2, EGTA 5, HEPES 10 (pH 7.2). The bath solution contained (in mM): NaCl 140, KCl 5, $MgCl_2$ 2, $CaCl_2$ 2, HEPES 10 (pH 7.3). Changes in extracellular pH were induced by shifting one out of six outlets of a microperfusion system in front of the cell or patch. Experiments were carried out at room temperature (20–24° C.).

II. Results

II.1 Purification

Screening of several tarantula venoms was carried out against cloned ASIC channels expressed in *Xenopus* oocytes. It singled out *Psalmopoeus cambridgei* venom as containing a potent inhibitor of the ASIC1a proton-gated current. A diluted solution of 1 μl crude venom (1:1000) applied to the oocyte, provoked a 90% block of the ASIC1a current. Separation led to the purification of the minor venom constituent Psalmotoxin 1 (PcTX1), in a two-step process (FIGS. 1A, B). PcTX1 is a 40-amino acid peptide, possessing 6 half-cysteines linked by three disulfide bridges. Its full sequence was established by the N-terminal Edman degradation of the reduced-alkylated toxin and of the several cleavage fragments. These fragments are shown in FIG. 1D. The calculated molecular weight (MW 4689.40 Da average) was in accordance with the measured MW (4689.25 Da) and suggested a free carboxylic acid at the C-terminal extremity.

PcTX1 has limited overall homology to other spider venom toxins identified to date. FIG. 1E shows a comparison between PcTX1 and other spider venom toxins. Homology varied from 55.6 to 68.9%. However, PcTX1 shares a conserved cysteine distribution found both in spider venom and cone snails and polypeptide toxins, as shown in FIG. 1F. PcTX1 is a basic (pI 10.38) polypeptide comprising nine basic and six acidic residues.

II.2 Synthesis

The chemical synthesis of PsTXI-OH unambiguously confirmed the structure of PcTX1. The purified refolded synthetic toxin (PcTX1s) and the native form have identical measured MW, and when co-injected in two separate experiments using reversed-phase and cation-exchange HPLC, native and synthetic PcTX1 were indistinguishable in their migration and co-eluted in both systems (FIG. 1C). Most electrophysiological experiments were, therefore. conducted with the synthetic toxin.

II.3 Selective Block of ASIC1a

The effect of PcTX1 on the activity of ASIC1a, ASIC1b, ASIC2a and ASIC3 channels expressed in *Xenopus laevi* oocytes is shown in FIG. 2. The natural as well as the synthetic toxin block the ASIC1a current recorded at pH 6, with an $IC_{50}$ of 0.9 nM (FIGS. 2A and B). The blockade is rapid and reversible. PcTX1 at a 10 nM concentration also completely blocks the ASIC1a current activated by a pH drop to pH 5 or pH 4 (not shown). PcTX1 is highly selective. Neither the native nor the synthetic PcTX1 (10 nM or 100 nM) blocked ASIC1b currents activated at pH 6 (FIG. 2C). Similarly, the ASIC2a channel activated by a pH drop to pH 5, was insensitive to the action of PcTX1 at 10 nM (FIG. 2D) or 100 nM (not shown). The rapid and slow components of the ASIC3 channel were also insensitive to the perfusion of PcTX1 at 10 nM (FIG. 2E) and 100 nM (not shown). The toxin was also tested on the epithelial ENaC channel formed by the assembly of alpha, beta and beta subunits and no inhibition occurred with concentrations of 10 nM or 100 nM PcTX1 (N=3, not shown).

Sequence homologies of PcTX1 with other spider toxins which block different subtypes of voltage-dependent $K^+$ channels, such as hanatoxins (Kv2.1), heteropodatoxins (Kv4.2) and phrixotoxins (Kv4.2, Kv4.3) (FIG. 1E), prompted testing of the affect of PcTX1 against Kv2.1, Kv2.2, Kv4.2 and Kv4-3 channels expressed in *Xenopus* oocytes. These channels were not affected by 10 nM or 100 nM PcTX1 (not shown).

Experiments carried out with the same ASIC channels expressed in COS cells confirmed the results obtained in oocytes. ASIC1a was completely inhibited by PcTX1, while ASIC1b, ASIC2a and ASIC3 were insensitive (N=10 for each channel) at the same toxin concentration (50 nM, not shown).

Figure 3:
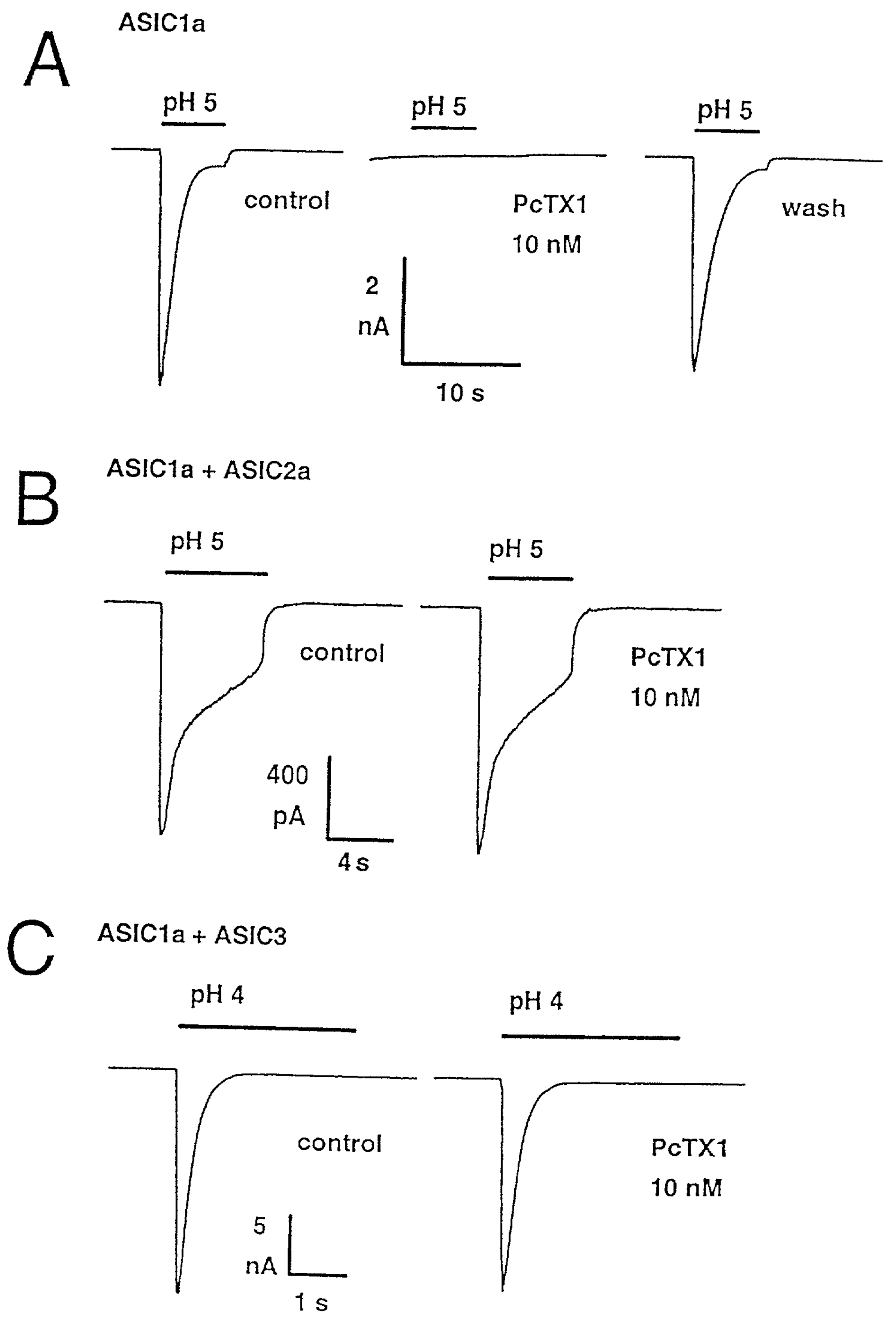
FIG. 3 has several parts relating to the effect of PcTX1 on homomultimers and heteromultimers. Part A is a graph demonstrating the effect of PcTX1 on the ASIC1a homomultimer. Part B is a graph showing the effect of PcTX1a on an ASIC1a+ASIC2a heteromultimer. Part C is a graph showing the effect of PcTX1a on an ASIC1a+ASIC3a heteromultimer.
Figure 8:
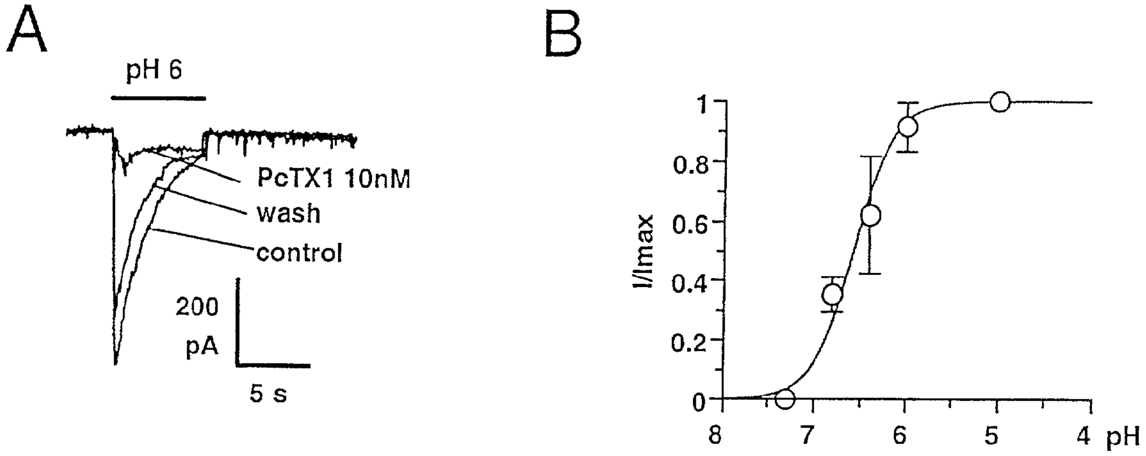

PcTX1 was then assayed on heteromultimers of the ASIC1a subunit (FIG. 3). Co-expression of ASIC1a and ASIC3 in COS cells produces a rapidly inactivating $H^+$-gated current (tau=0.19±0.01 s at pH 6, N=5) that is insensitive to PcTX1 (N=10) (FIG. 3C), while ASIC1a homomultimers produce a current which inactivates more slowly at the same pH 6 (tau=2.10±0.30 s, N=10), but which is completely blocked by PcTX1 (10 nM) (FIG. 3A). ASIC1a/ASIC2a heteromultimers were also insensitive to PcTX1 (FIG. 3B), demonstrating the specificity of PcTX1.

The ASIC1a channel can also be blocked by amiloride, but the $IC_{50}$ is 10 μM, i.e., $10^4$ lower in affinity than PcTX1. Moreover, amiloride is not selective. It blocks all transient expression of current generated by ASIC1a, ASIC1b, ASIC2a, and ASIC3. Amiloride also inhibits epithelial $Na^+$ channels, the FMRFamide $Na^+$ channel, T-type $Ca^{2+}$ channels and many other transport systems such as the $Na^+$/H+ and $Na^+/Ca^{2+}$ exchangers.

II.4 Activity of PcTX1 on Native Proton-gated Currents

The small dorsal root ganglion (DRG) neurons isolated from 2 day-old rats were voltage-clamped at −60 MV and stimulated by a pH drop from pH 7.3 to pH 6. As previously observed in small sensory neurons in trigeminal ganglia, this pH change evoked three different types of responses which are presented in FIGS. 4A–C. Currents presented in FIG. 4A were blocked by 3–10 nM of the toxin PcTX1, while $H^+$-evoked currents in other neurons were insensitive to the toxin (FIGS. 4B–C). DRG neurons express at least two subpopulations of transient currents as judged by their constants of inactivation (FIGS. 4A–B, 4D). One population inactivates very rapidly with a time constant of inactivation below 0.5 s, while the other one has time constants between 1 and 3 s, the average time constant of inactivation being 1.95±0.14 s (N=23). The data clearly indicate that the most rapidly inactivating currents with an average time constant of inactivation of 0.24±0.03 s (N=22) are insensitive to PcTX1. Only the more slowly inactivating H+ channels are highly sensitive to PcTX1.

The dose-response curve presented in FIG. 4E was obtained from the PcTX1-sensitive population of neurons. The $IC_{50}$ value for half-maximum inhibition is 0.7 nM, very similar to the value of 0.9 nM obtained for ASIC1a channels expressed in *Xenopus* oocytes.

FIG. 4F shows that a change of the extracellular pH from pH7.3 to pH6 in neurons that express the channel type shown in FIG. 4A evokes a rapid depolarization resulting in a train of action potentials. This effect is blocked by very low concentrations of PcTX1 and this inhibition is reversible, as shown in the return to control behavior after washing.

ASIC channel subunits are highly expressed in cerebellum and particularly in granular cells. This is why these cells were used to analyze the properties of these channels in CNS neurons (FIG. 5). Cerebellar granule cells in culture all responded to a pH drop from pH 7.3 to pH 6 with a transient $Na^+$ inward current characterized by a time constant of inactivation of 2.06±0.17 s, (N=10) (FIG. 5A). Both the rate of inactivation and the pH dependence of this $H^+$-gated $Na^+$ channel ($pH_{0.5}$ 6.6 versus $pH_{0.5}$ 6.4) are very similar to those of the ASIC1a channel (FIG. 5B). $H^+$-gated $Na^+$ channels with the same properties have been recently identified in cortical neurons. The transient $H^+$-gated $Na^+$ channel expressed by granule cells was completely inhibited by 10 nM PcTX1 (N=10) (FIG. 5A).

The invention claimed is:

1. A method of manufacturing an ASIC1a channel blocker comprising the steps of:

(a) obtain at least one *Psalmopoeus cambridgei* spider;

(b) obtaining venom from said spider by electrically milking said spider;

(c) separating toxins of said venom by reversed-phase chromatography;

(d) further separating components of said venom by cation exchange chromatography;

(e) recovering and isolating separated toxins of said venom; and (f) combining said isolated toxin with a pharmaceutically acceptable carrier such that the toxin is capable of functioning as an ASIC1a channel blocker.

2. A substantially pure polypeptide functioning as an ASIC1a channel blocker and comprising the following amino acid sequence:

EDCIPKWKGCVNRHGDCCE-GLECWKRRRSFEVCVPKTPKT SEQ ID NO:1 and pharmaceutically-acceptable salts thereof.

3. The substantially pure polypeptide defined in claim 2 comprising the following amino acid sequence:

EDCIPKWKGCVNRHGDCCE-GLECWKRRRSFEVCVPKTPKT SEQ ID NO:1.

4. The substantially pure polypeptide as defined in claim 2, wherein the polypeptide has a calculated molecular weight of about 4689.

5. A substantially pure compound comprising the following amino acid sequence:

EDCIPKWKGCVNRHGDCCE-GLECWKRRRSFEVCVPKTPKT SEQ ID NO:1.

6. A peptide isolated from the venom of the *Psalmopoeus cambridgei* spider and comprising the following amino acid sequence:

EDCIPKWKGCVNRHGDCCE-GLECWKRRRSFEVCVPKTPKT SEQ ID NO:1.

7. A composition containing a polypeptide comprising the following amino acid sequence:

EDCIPKWKGCVNRHGDCCE-GLECWKRRRSFEVCVPKTPKT SEQ ID NO:1 or salts thereof and a pharmaceutically-acceptable carrier.

8. A composition functioning as an ASIC1a channel blocker comprising at least one toxin extracted from the *Psalmopoeus cambridgei* spider, said at least one toxin being capable of functioning as an ASIC1a channel blocker.

9. A composition as defined in claim 2, wherein the effets of said at least one toxin are reversible.

10. A substantially pure polypeptide functioning as an ASIC1a channel blocker which is manufactured by a) obtaining at least one *Psalmonoeus cambridgei* spider; (b) obtaining venom from said spider by electrically milking said spider; (c) separating toxins of said venom by reverse-phase chromatography; (d) further separating components of said venom by cation exchange chromatography; (e) recovering and isolating separated toxins of said venom to obtain the substantially pure polypeptide.

11. A substantially pure polypeptide functioning as an ASIC1a channel blocker of claim 10 having a calculated molecular weight of about 4689 Da.

12. A substantially pure polypeptide functioning as an ASIC1a channel blocker comprising an amino acid sequence represented by SEQ ID NO: 1 or pharmaceutically-acceptable salts thereof.

* * * * *